United States Patent [19]

Suh

[11] Patent Number: 5,476,881
[45] Date of Patent: Dec. 19, 1995

[54] ANTIMICROBIAL COMPOSITION FOR MANUFACTURING NIPPLES

[76] Inventor: Kang I. Suh, No. 217-701, Sinsigaji Apt. 902, Mok-dong, Yangcheon-ku Seoul, Rep. of Korea

[21] Appl. No.: 469,631

[22] Filed: Jun. 6, 1995

Related U.S. Application Data

[63] Continuation-in-part of Ser. No. 179,674, Jan. 11, 1994, abandoned.

[30] Foreign Application Priority Data

Feb. 15, 1993 [KR] Rep. of Korea ............... 1993-2040

[51] Int. Cl.$^6$ ............... C08K 13/02; A61J 11/00
[52] U.S. Cl. ............... 523/122; 106/15.05; 215/11.1; 524/403; 606/236
[58] Field of Search ............... 106/15.05; 523/122; 215/11.1; 606/236; 524/403, 430, 442

[56] References Cited

U.S. PATENT DOCUMENTS

| | | | |
|---|---|---|---|
| 4,078,566 | 3/1978 | Urban, Jr. ............... | 128/252 |
| 4,195,639 | 4/1980 | Lee ............... | 128/481 |
| 4,731,348 | 3/1988 | Gonzales-Oliver ............... | 501/37 |
| 4,849,223 | 7/1989 | Pratt et al. ............... | 424/409 |
| 4,906,466 | 3/1990 | Edwards et al. ............... | 424/421 |
| 4,917,252 | 4/1990 | Chambers et al. ............... | 215/11.1 |
| 5,004,473 | 4/1991 | Kalantar ............... | 215/11.1 |
| 5,108,686 | 4/1992 | Griffin ............... | 215/11.1 |
| 5,322,031 | 6/1994 | Lerner et al. ............... | 606/234 |
| 5,328,954 | 7/1994 | Sarangapani ............... | 524/589 |
| 5,338,565 | 8/1994 | Shlenker et al. ............... | 606/236 |

FOREIGN PATENT DOCUMENTS

| | | | |
|---|---|---|---|
| 40-14308 | 7/1965 | Japan ............... | 501/68 |
| 1-238508 | 9/1989 | Japan . | |
| 2-215794 | 8/1990 | Japan . | |
| 2-268104 | 11/1990 | Japan . | |
| 4-46106 | 2/1992 | Japan . | |
| 4-288006 | 10/1992 | Japan . | |

*Primary Examiner*—Anthony Green
*Attorney, Agent, or Firm*—Nixon & Vanderhye

[57] ABSTRACT

Disclosed herein is an antimicrobial composition for manufacturing nipples, which comprises 40–80% by weight of silicon oxide, 20–50% by weight of aluminum oxide and 1–10% by weight of silver or silver oxide. Further is disclosed a sanitized nipple which is made from silicone or latex to which is incorporated said composition.

1 Claim, No Drawings

ANTIMICROBIAL COMPOSITION FOR MANUFACTURING NIPPLES

This is a continuation-in-part of application Ser. No. 08/179,674, filed Jan. 11, 1994, now abandoned.

BACKGROUND OF THE INVENTION

1. Field of the Invention

The present invention is related to a composition for manufacturing nipples, and more particularly it is related to an antimicrobial composition which is employed for manufacturing nipples.

2. Prior Arts

Vented nipples for nursing bottle or non-vented nipples are made from latex or silicone resin and have been disinfected by boiling, or with steam or a disinfecting tablet. However, because the nursing bottles which contain milk or other beverages are commonly allowed to stand in the air, the nipples thereof are exposed to a contamination by various bacteria or other pathogenic microorganisms. Consequently, when babies are nourished with milk using these nourishing bottles, they frequently suffer from diarrhea or other infective diseases.

Therefore, there has been a need to provide vented or non-vented nipples which can be allowed to stand in the air without a possibility of being contaiminated with microorganisms.

SUMMARY OF THE INVENTION

Accordingly, an object of the invention is to provide a antimicrobial composition for manufacturing nipples.

Another object of the invention is to provide a antimicrobial composition for manufacturing nipples, which comprises 40–79% by weight of silicon oxide, 20–50% by weight of aluminum oxide and 1–10% by weight of silver or silver oxide.

Another object of the invention is to provide a sanitized nipple which is made from a mixture consisting of 100 parts by weight of silicone or latex and 0.2 to 1 part by weight of an antimicrobial composition which comprises 40–79% by weight of silicon oxide, 20–50% by weight of aluminum oxide and 1–10% by weight of silver or silver oxide.

DETAILED DESCRIPTION OF THE INVENTION

The antimicrobial composition of the present invention comprises 40–79% by weight of silicon oxide, 20–50% by weight of aluminum oxide and 1–10% by weight of silver or silver oxide.

The present inventor had made extensive researches to find out a composition which shows antimicrobial activity as well as can be safely used as a material for manufacturing nipples. As a result thereof, I found that the combination of silicon oxide and aluminum oxide is capable of inhibiting growth of microbials whilst has no adverse effect to babies. This found is an unexpected result because silicon oxide or aluminum oxide itself does not show any antimicorbial activity.

The ratio of silicon oxide to aluminum oxide is not particularly restricted and preferably ranges between 0.5 and 4.

Further, the antimicrobial activity of the combination of silicon oxide and aluminum oxide cart be increased by adding silver or silver oxide. Silver or silver oxide may be added in an amount of 1–10% by weight based on the total weight of the composition.

Therefore, the composition of the invention comprises 40–79% by weight of silicon oxide, 20–50% by weight of aluminum oxide and 1–10% by weight of silver or silver oxide.

The composition of the present invention may be incorporated into silicone or latex which is usually employed for manufacturing nipples in an mount of 0.2–1 part by weight. The silicone or latex mixed with the composition of the present invention may be subjected to conventional injection or pressure molding to produce nipples.

Thus produced nipples have antimicrobial activity and therefore may be used hygienically.

The present invention will be described in more detail by way of the following non-limitative Examples.

EXAMPLE 1

2 g of the composition consisting of silicon oxide 0.9 g, aluminum oxide 1.08 g and silver 0.02 g was added to 1000 g of silicone resin and the resulting mixture was subjected to injection molding to produce vented silicone nipples.

EXAMPLE 2

10 g of the composition consisting of silicon oxide 6 g, aluminum oxide 3.3 g and silver oxide 0.7 g was added to 1000 g of silicone resin and the resulting mixture was subjected to pressure molding to produce non-vented silicone nipples.

EXPERIMENTAL EXAMPLE

Using non-vented nipples containing 0.2 and 1 part by weight of the antimicrobial composition, respectively and a conventional silicone non-vented nipple, the following experiment was carried out.

A loopful of test organisms was placed in the nipples to be tested and the open ends of the nipples were heat sealed. The nipples were allowed to stand under the pressure for 24 hours and inside of the nipples was rinsed off with a physiological saline. The resulting washings were inoculated into a nutrient agar plate and incubated at 37° C. for 24 hours. Alter the incubation, the number of cells on the plate were counted. The total number of cells was calculated by producing the number of cells counted by the dilution ratio. The results are shown in Table 1.

TABLE 1

| Strains | Nipples | Unit | Initial Conc. | 24 hours later | Inhibition (%) |
|---|---|---|---|---|---|
| Staphylococcus aureus | Containing 0.2 part Containing | Cells/cc | $1.6 \times 10^4$ $1.6 \times 10^4$ | $9.6 \times 10^2$ $2.3 \times 10^2$ | 94.5 98.6 |

TABLE 1-continued

| Strains | Nipples | Unit | Initial Conc. | 24 hours later | Inhibition (%) |
|---|---|---|---|---|---|
| ATCC 25923 | 1 part Conventional | | $1.6 \times 10^4$ | $1.2 \times 10^4$ | 25 |
| E. coli ATCC 25922 | Containing 0.2 part | Cells/cc | $1.3 \times 10^3$ | $6.5 \times 10^1$ | 95.5 |
| | Containing 1 part | | $1.3 \times 10^3$ | $2.1 \times 10^1$ | 98.4 |
| | Conventional | | $1.3 \times 10^3$ | $1.0 \times 10^3$ | 23.1 |

I claim:

1. A sanitized nipple made from a mixture consisting of 100 parts by weight of silicone or latex and 0.2 to 1 part by weight of an antimicrobial composition which comprises 40–79% by weight of silicon oxide, 20–50% by weight of aluminum oxide and 1–10% by weight of silver or silver oxide.

* * * * *